(12) United States Patent
Said

(10) Patent No.: US 11,864,952 B2
(45) Date of Patent: Jan. 9, 2024

(54) TISSUE EXPANDER

(71) Applicant: Hakim Said, Mercer Island, WA (US)

(72) Inventor: Hakim Said, Mercer Island, WA (US)

( * ) Notice: Subject to any disclaimer, the term of this patent is extended or adjusted under 35 U.S.C. 154(b) by 751 days.

(21) Appl. No.: 16/667,202

(22) Filed: Oct. 29, 2019

(65) Prior Publication Data

US 2020/0129260 A1 Apr. 30, 2020

Related U.S. Application Data

(60) Provisional application No. 62/751,999, filed on Oct. 29, 2018.

(51) Int. Cl.

| | | |
|---|---|---|
| *A61B 90/00* | (2016.01) | |
| *A61F 2/12* | (2006.01) | |
| *A61M 25/10* | (2013.01) | |
| *A61B 17/00* | (2006.01) | |

(52) U.S. Cl.
CPC .............. *A61B 90/02* (2016.02); *A61F 2/12* (2013.01); *A61M 25/10181* (2013.11); *A61B 2017/00796* (2013.01)

(58) Field of Classification Search
CPC . A61B 90/02; A61B 2017/00796; A61F 2/12; A61M 25/10181
See application file for complete search history.

(56) References Cited

U.S. PATENT DOCUMENTS

| | | | | |
|---|---|---|---|---|
| 3,919,724 | A * | 11/1975 | Sanders | A61F 2/12 623/8 |
| 5,993,473 | A * | 11/1999 | Chan | A61F 5/003 606/191 |
| 6,540,764 | B1 * | 4/2003 | Kieturakis | A61B 17/00234 606/151 |
| 2005/0192668 | A1 * | 9/2005 | Studin | A61F 2/12 623/8 |
| 2010/0063530 | A1 * | 3/2010 | Valencon | A61F 5/003 606/192 |
| 2017/0348089 | A1 * | 12/2017 | Becker | A61F 2/12 |

* cited by examiner

*Primary Examiner* — Todd J Scherbel
(74) *Attorney, Agent, or Firm* — Hamre, Schumann, Mueller & Larson, P.C.

(57) ABSTRACT

A minimally invasive medical device for tissue expansion is provided. The medical device has an expandable balloon and a sturdy substantially hollowed core. A membrane-covered port is provided at one end of the balloon to receive an insertion apparatus or an injection member. The balloon is inflatable by injecting a gas or a liquid through the membrane-covered port via the insertion apparatus or the injection member. A shell is provided to substantially encase the balloon and the insertion apparatus is provided to assist with maneuverability of the medical device. A method of tissue expansion includes implanting the medical device into an expandable tissue and inflating the balloon. A method of expanding a breast tissue of a patient after a mastectomy includes placing a patient under local anesthesia, making a small incision into an expandable tissue, implanting the minimally invasive medical device, and inflating the device gradually.

20 Claims, 6 Drawing Sheets

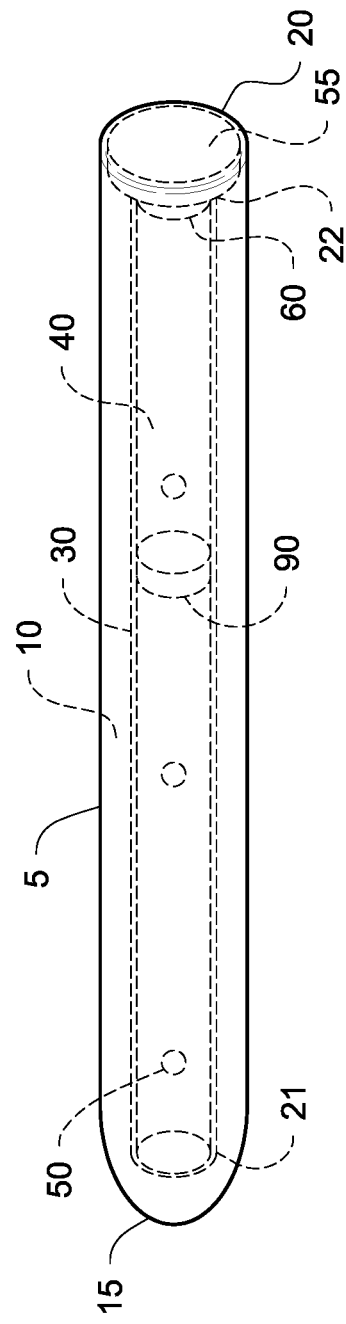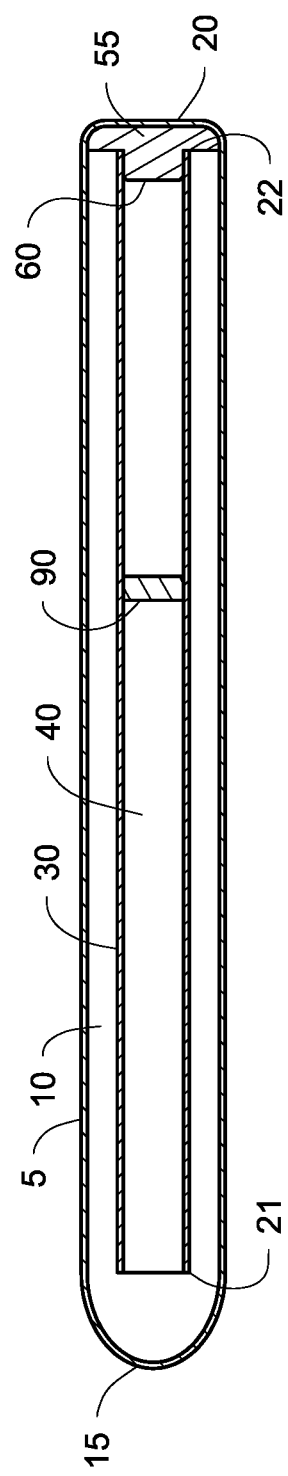

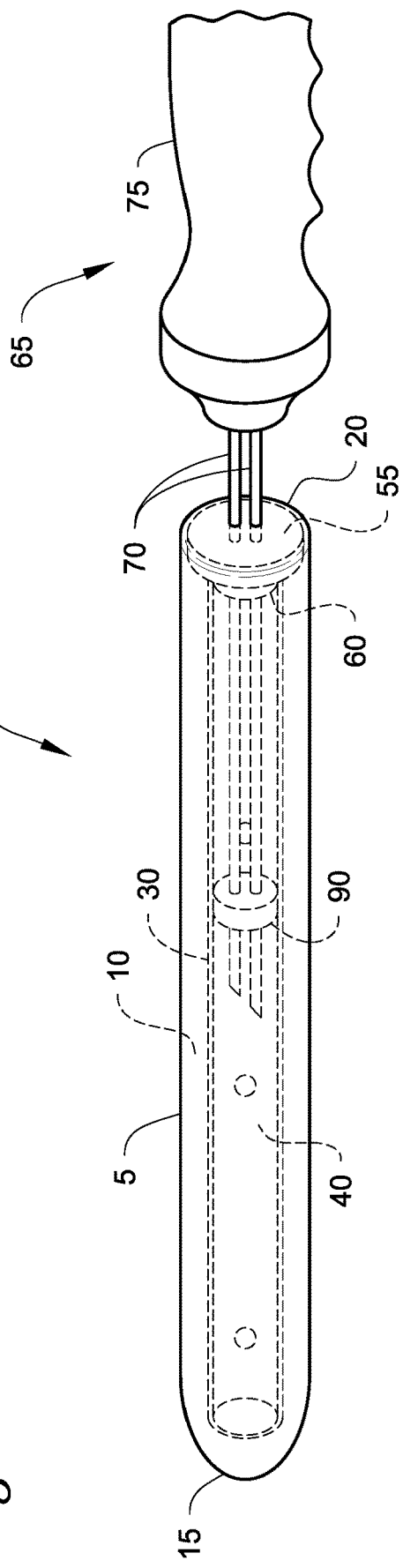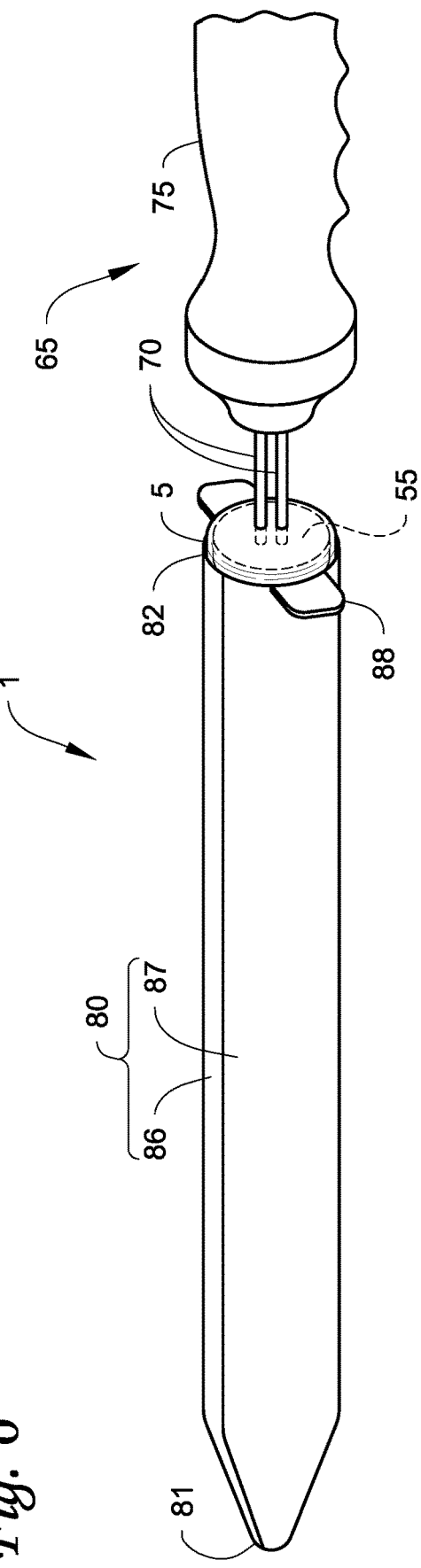

TISSUE EXPANDER

FIELD OF THE DISCLOSURE

The embodiments recited and described herein pertain to the gradual expansion of tissues of a patient during a medical procedure.

BACKGROUND

Plastic surgery after excision of a tissue, such as removal of a cancerous tumor, has become a common procedure as the survival rate of patients after surgery has increased. Breast reconstruction after a mastectomy, in particular, has been in high demand as increasing number of patients live many years after a mastectomy and wish to regain the breast shape that was lost to surgery.

In general, for breast reconstruction surgery after mastectomy, a sealed inflatable device is implanted into the breast, and overlying tissue is expanded by gradually inflating the device over the course of several months. After the tissue has been expanded to the desired size, the inflatable device is replaced with a permanent prosthetic.

Currently available tissue expanders are disc shaped and require a large incision, with the patient being placed under general anesthesia for the implantation. Such implantation procedures incur an economical and physical burden to the patient after a mastectomy, and has actually deterred some patients from choosing breast reconstruction.

BRIEF DESCRIPTION OF THE DRAWINGS

The accompanying drawings illustrate various embodiments of the medical device, methods, and various other aspects of the disclosure. While multiple embodiments are disclosed, still other embodiments of the present disclosure will become apparent to those skilled in the art from the following detailed description. As will be realized, the disclosure can be modified in various aspects, all without departing from the spirit and scope of the present disclosure. It may be that in some examples one element may be designed as multiple elements or that multiple elements may be designed as one element. Furthermore, elements may not be drawn to scale. The components in the figures are not necessarily to scale, emphasis instead being placed upon illustrating principles. Accordingly, the drawings and detailed description are to be regarded as illustrative in nature and not restrictive.

FIG. 1 is a lateral-proximal perspective view of the medical device, in accordance with at least one embodiment described herein.

FIG. 2 is a lateral cross-sectional view of the medical device shown in FIG. 1.

FIG. 5 is a lateral view of the medical device with an insertion apparatus attached, in accordance with at least one embodiment described herein.

FIG. 6 is a lateral view of the medical device of FIG. 5 when the distal end of the shell is separated.

LEGENDS TO THE FIGURES

Figure 3:
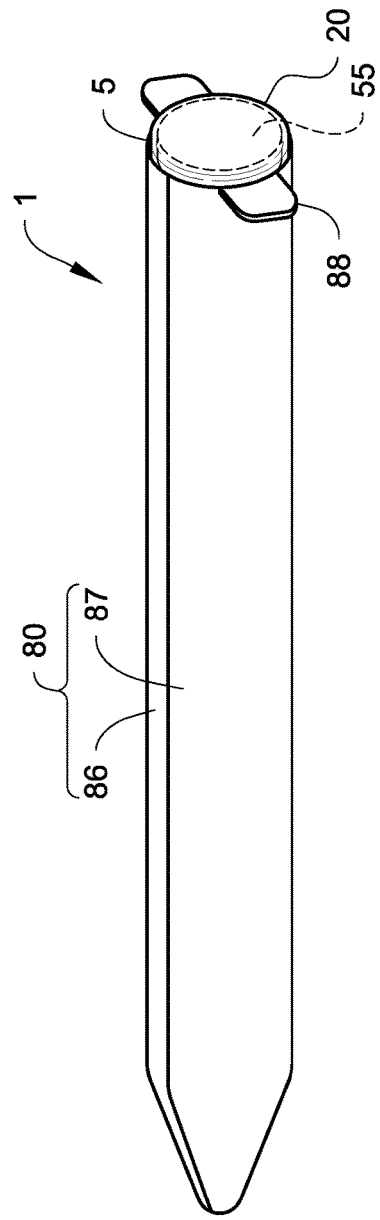
FIG. 3 is a lateral-proximal perspective view of the medical device, in accordance with at least one embodiment described herein.

Like reference numbers represent like parts throughout.
 1: medical device
 5: balloon
 10: inner space of balloon
 15: first longitudinal end of balloon
 20: second longitudinal end of balloon
 21: first longitudinal end of core
 22: second longitudinal end of core
 30: core
 40: second inner space of core
 50: hole
 55: membrane-covered port
 56: suture
 57: projecting tab
 60: port
 65: insertion apparatus
 70: insertion member
 71: injection member
 75: handle
 80: shell
 81: first longitudinal end of shell
 82: second longitudinal end of shell
 86: first half of shell
 87: second half of shell
 88: tab
 90: self-sealing gel
 95: laminated back shell and core

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

Unless the context clearly requires otherwise, throughout the description and the claims, "Disposed" is used to indicate a state of a subject, including, but not limited to, being provided, attached, connected, associated, bonded, and welded, and does not particularly limit the method of connection or directness or indirectness of the connection.

The meaning of "corresponding" as used in this disclosure includes, in addition to dictionary definitions, "having the same or nearly the same positional relationship," "analogous or equivalent in relative position," and "accompanying."

The subject matter recited and described herein may reference different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

EMBODIMENTS

FIG. 1 is a lateral-proximal perspective view of the medical device in accordance with at least one embodiment. The medical device (1) has an expandable balloon (5) and a substantially hollowed core (30). The expandable balloon (5) has an inner space (10), a first longitudinal end (15), a second longitudinal end (20), and a membrane-covered port (55) at the second longitudinal end of the balloon (20).

The core (30) has a second inner space (40), a first longitudinal end of the core (21) corresponding to the first longitudinal end of the balloon (15), a second longitudinal end of the core (22) corresponding to the second longitudinal end of the balloon (20), and a port (60) at the second longitudinal end of the core (22). The membrane-covered port (55) and the port (60) may be a self-sealing gel. Additional self-sealing gel (90) can optionally be disposed in the middle portion of the core (30). The core (21) has at least one hole (50) configured as a conduit between the inner space of the balloon and the inner space of the core.

The size of the balloon (5) may be configured to match the size of the tissue to be expanded. For breast tissue expansion in the context of breast reconstruction surgery after a mastectomy, the balloon may be, for example, about 10-about 14 cm in length and about 1 cm in diameter. The size of the balloon (5) may be adjusted according to the body size of the patient, among other factors. The core is made of a stiff plastic material that is suitable for insertion into medical tissue. The self-sealing gel material used for the membrane-covered port (55), the port (60) and additional self-sealing gel (90) may be a medically suitable silicone gel, such as those used to enable needle access in central venous catheters, antibiotic infusion ports, gastric band ports, etc.

FIG. 2 is a lateral cross-sectional view of the medical device in the embodiment of FIG. 1. The membrane-covered port (55) and the port (60) are disposed at the second longitudinal end of the balloon (20) and second longitudinal end of the core (22), respectively; and may be formed and disposed separately, formed separately and bonded together, or formed in one piece.

FIG. 3 is a lateral-proximal perspective view of the medical device (1) in the embodiment of FIG. 1. The shell (80) is configured to substantially encase the balloon (5) when the balloon is in a deflated state. The shell (80) has a first longitudinal end (81) corresponding to the first longitudinal end of the balloon (15) and a second longitudinal end (82) corresponding to the second longitudinal end of the balloon (20). The shell (80) has at least one tab (88) disposed at the second longitudinal end of the shell (82). The first longitudinal end of the balloon (15) is covered by the shell (80), and the shell (80) may be separated into a first half (86) and a second half (87) longitudinally.

The shell (80) is made of a surgically suitable sturdy material including, for example but not as a limitation, a silicone or silastic material, and may protect the balloon (5) from being damaged during implantation into a subject's tissue. The outer surface of the shell (80) is puncture-proof and may be smooth or textured. The shell (80) may be longitudinally separated into two or more pieces. The manner in which the shell (80) is separated may be modified to different shapes or number of pieces. The shell (80) may have a tab (88) to assist with maneuvering of the medical device and separation of the shell.

Figure 4A:
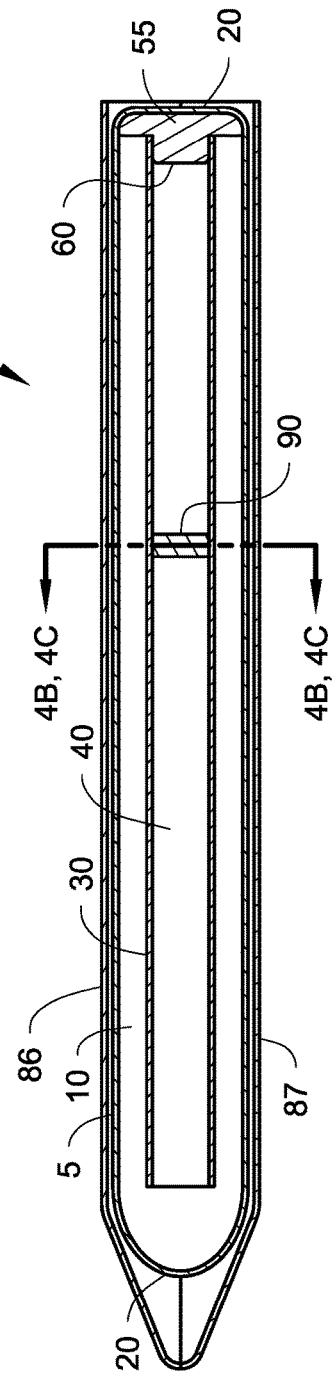
FIG. 4A is a longitudinal cross-sectional view of the medical device shown in FIG. 3.

FIG. 4A is a longitudinal cross-sectional view of the medical device (1) in the state shown in FIG. 3. The shell (80) snugly covers a substantial portion of the balloon (5) in a deflated state.

Figure 4B:
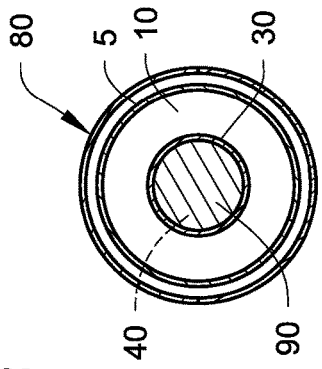
FIG. 4B is a proximal transverse sectional view of the medical device shown in FIG. 3.

FIG. 4B is a transverse section of one embodiment of the medical device (1) along the line indicated in FIG. 4A. The shell (80), the balloon (5), and the core (10) may be substantially concentric, and may have a self-sealing gel (60) inside the second inner space (40). The balloon (80) may be substantially circular in the transverse section and expandable in multiple directions.

Figure 4C:
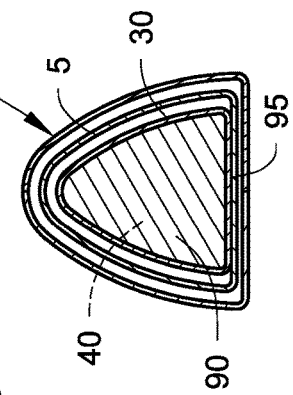
FIG. 4C is a proximal transverse sectional view of the medical device shown in FIG. 3.

FIG. 4C is a transverse section of the medical device (1) along the line indicated in FIG. 4A, in accordance with another embodiment. The balloon (80) may be provided having a predetermined shape in the transverse section, and may be inflatable in predetermined directions. In at least one embodiment, the balloon (80) may be configured to expand into a shape suitable for breast reconstruction. The balloon (80) may have a laminated back shell and core (95) or the like that aids in positioning of the medical device (1) when placed in a tissue, and be configured for directional inflation.

Figure 4D:
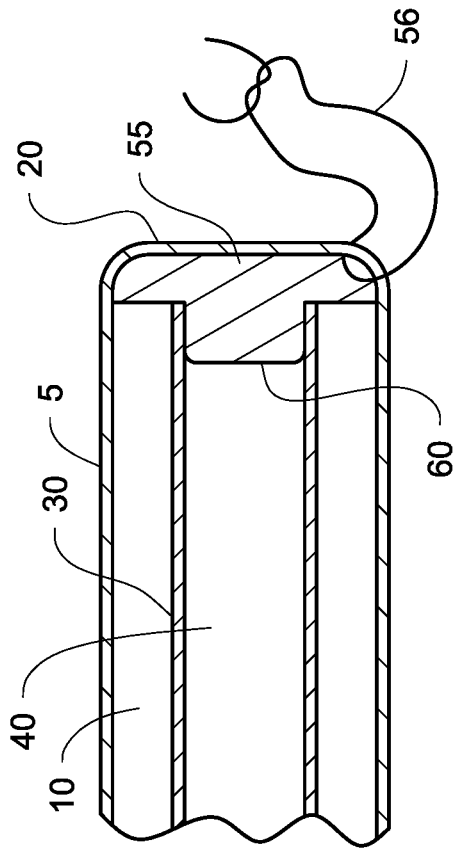
FIG. 4D is an enlarged lateral cross sectional view of the proximal portion of the medical device shown in FIG. 3.

FIG. 4D is an enlarged lateral cross sectional view of the proximal portion of the medical device (1) in accordance with one example embodiment showing a suture (56) attached to the device. The suture (56) may be attached to the balloon (5) and the membrane-covered port (55) to limit the movement of the medical device (1) after being implanted into a tissue.

Figure 4E:
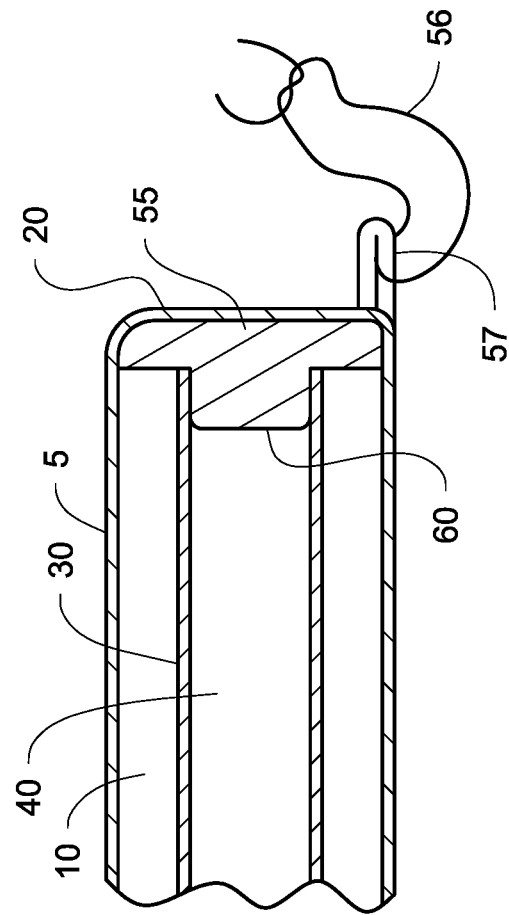
FIG. 4E is and enlarged lateral cross sectional view of the proximal portion of the medical device shown in FIG. 3.

FIG. 4E is an enlarged lateral cross sectional view of the proximal portion of the medical device (1) in another example embodiment showing a suture (56) attached to the device. A projecting tab (57) can be formed at the second longitudinal end of the balloon (20) as a conduit to allow fixation of a suture (56).

FIG. 5 is a lateral-proximal perspective view of the medical device (1) in accordance with at least one example embodiment. The insertion apparatus (65) is attached. The shell (80) is not shown. In this embodiment, the insertion apparatus (65) has a handle (75) and two insertion members (70) that pierce the membrane-covered port (55) disposed at the second longitudinal end of the balloon, the port (60) disposed at the second longitudinal end of the core, and the self-sealing gel (90) disposed at a middle portion of the inner space of the core. The insertion members (70) connect with the inner space (40) of the core (30).

The material of the insertion members (70) is, for example, a 21 gauge needle. The handle (75) may be used to guide the piercing of the membrane-covered port (55), the port (60), and the self-sealing gel (90) by the insertion members (70). When the insertion apparatus is engaged with the membrane-covered port (55), the port (60), and an optional self-sealing gel (90), the self-sealing gels placed at these positions limit the movement of the insertion member. The handle (75) may also be used to maneuver the medical device (1) during an implanting procedure of the medical device (1) into the tissue of the subject. The handle (75) may be further configured to control removal of the implanted medical device (1) from the tissue. The insertion members (70) may also be used to inject gas or liquid into the inner space of the core (40).

FIG. 6 is a lateral-proximal perspective view of the medical device (1) in accordance with at least one example embodiment. The shell (80) and the insertion apparatus (65) are shown. The shell (80) substantially encases the balloon (5). The insertion members (70) pierce the membrane-covered port (55) and connect with the balloon (5) and the core (30). During the procedure of implanting the medical device (1) into a tissue, the rigid shell (80) protects the balloon (5) from being damaged, and the handle (75) may be used to assist with the insertion and/or removal of the medical device (1) into/from the tissue.

Figure 7:
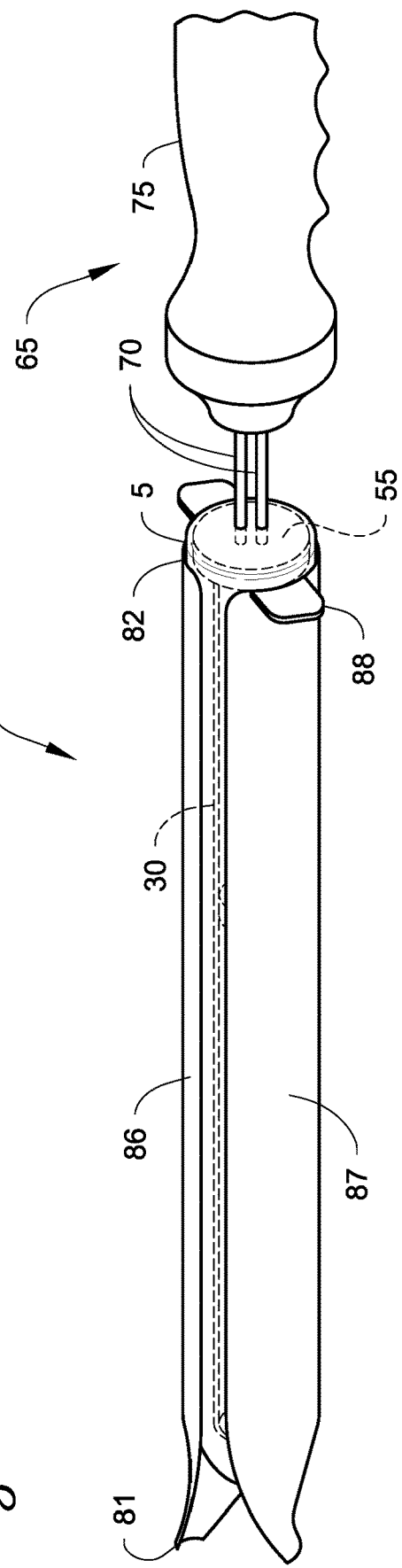
FIG. 7 is a lateral view of the medical device of FIG. 5 t when the shell is separated into two halves.

FIG. 7 is a lateral-proximal perspective view of the medical device (1) in accordance with at least one example embodiment when the insertion apparatus (65) is attached, and shell (80) is separated into two halves (86 and 87). After the medical device (1) is placed in the desired place in the target tissue, the shell (80) may be separated into smaller pieces by operating the tab (88) and removed from the medical device (1) and from the tissue. This allows proper placement of the medical device (1) into the target tissue without damaging the balloon (5).

Figure 8:
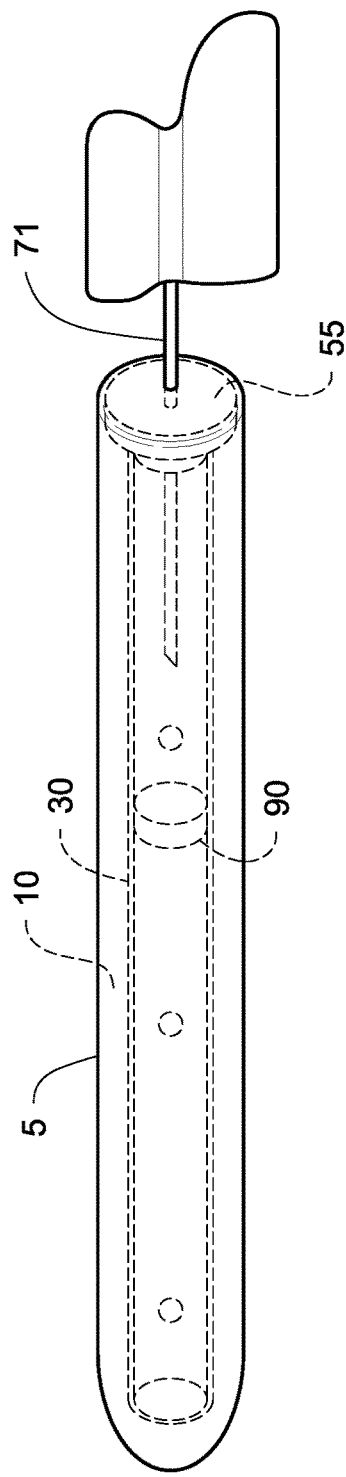
FIG. 8 is a lateral view of the medical device of FIG. 5 with an injection member attached.

FIG. 8 is a lateral-proximal perspective view of the medical device (1) in one embodiment when receiving an injection member (71). An example with a butterfly needle is shown; however the injection member may be any other medically suitable conduit to inject a gas or a liquid, including a needle and a catheter. In this embodiment, the inner space of the core (40) is receiving the injection member (71). A gas or a liquid can be injected into the inner space of the core (40) via the injection member (71), and then move into the inner space of the balloon (10) via at least one hole (50) to inflate the balloon (5).

Figure 9:
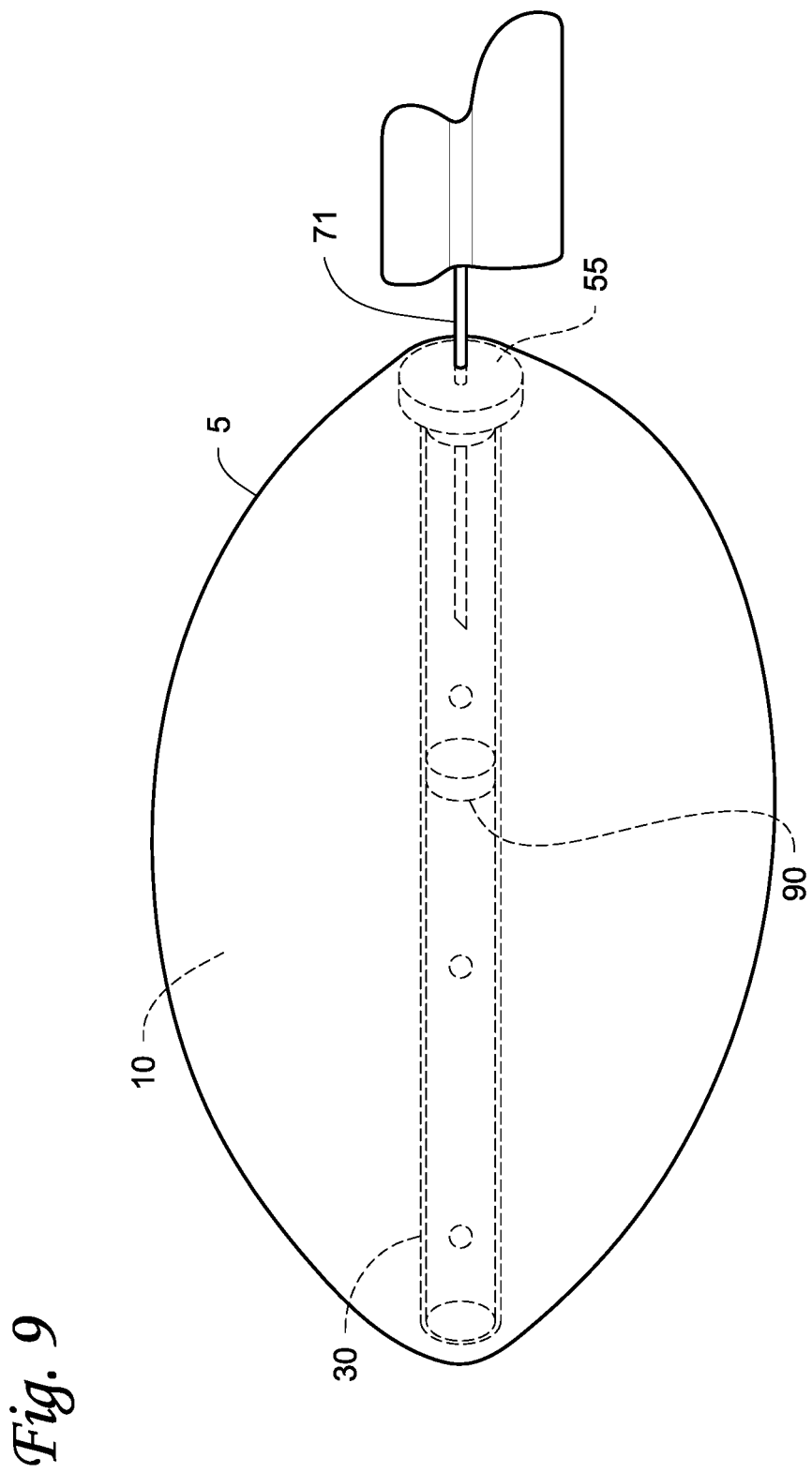
FIG. 9 is a lateral view of the medical device of FIG. 5 when the balloon is expanded.

FIG. 9 is a lateral-proximal perspective view of the medical device (1) in accordance with at least one example embodiment when receiving an injection member (71) and the balloon (5) has been expanded. A gas or a liquid can be injected via the injection member (71), and move from the inner space of the core (40) into the inner space (10) to inflate the balloon (5). The medical device (1) can receive the gas or the liquid after being implanted into the tissue.

EXAMPLES

Example 1

In one example, the medical device (1) may be implanted after mastectomy, after the surgical wound has healed. The procedure may include:
giving a local anesthesia to the expandable tissue of a patient under sterile condition, making a minimal-length incision just enough to insert the medical device (1) into the tissue;
inserting the at least one insertion member (70) into the balloon (5) of the medical device via the membrane-covered port (55) that is exposed from the shell (80);
inserting the medical device (1) with a shell (80) into the tissue of the patient by operating the handle (75) of the insertion apparatus (65);
separating the shell (80) into the first half (86) and the second half (87) by operating the tab (88);
removing the first half (86) and the second half (87) of the shell from the tissue;
removing the insertion apparatus (65) from the medical device (1);
suturing the incision, leaving the balloon (5) inside the tissue.

The length of the incision may be adjusted such as to allow insertion of the shell (80) from the distal end into the tissue. The length of the incision is from about 0.8 cm to about 2.0 cm, for example, about 1.2 cm.

Example 2

In another example, the medical device (1) may be implanted immediately after mastectomy, when the patient has been given general anesthesia. The procedure may include:
inserting the at least one insertion member (70) into the balloon (5) of the medical device via the membrane-covered port (55) that is exposed from the shell (80);
placing the medical device (1) with a shell (80) into the tissue of the patient by operating the handle (75) of the insertion apparatus (65);
separating the shell (80) into the first half (86) and the second half (87) by operating the tab (88);
removing the first half (86) and the second half (87) of the shell from the tissue; removing the insertion apparatus (65) from the medical device (1); and
suturing the incision, leaving the balloon (5) inside the tissue.

Example 3

In yet another example, the medical device (1) may be implanted without using the insertion apparatus (65) and the shell (80) immediately after mastectomy, when the incision is large. The patient has been given general anesthesia. The operator may directly place the balloon (5) into the expandable tissue.

Example 4

In operation, the medical device (1) may be tethered to the surrounding tissue, such as connective tissue or muscle to prevent an undesired shifting of the medical device (1). A suture (56) may be attached to the balloon (5) and the membrane-covered port (55) or to a projecting tab (57) and tied to the surrounding tissue.

Example 5

In operation, the medical device (1) may be expanded after implantation. The procedure can be done in clinics or by a qualified medical practitioner visiting the patient, and may include:
  sterilizing the patient's skin covering the membrane-covered port (55),
  inserting the at least one insertion member (70) or an injection member (71) into the membrane-covered port (55) such that the at least one insertion member (70) or an injection member (71) connects with the second inner space of the substantially hollowed core (40); and
  injecting an externally-provided gas and/or a liquid through the at least one insertion member or an injection member into the second inner space of the substantially hollowed core.

Examples of gas include room air and sterilized room air. Examples of liquid include saline, colored saline, and saline supplemented with an antibiotic. The injection member (71) may be any medically suitable conduit, such as a needle or a syringe.

Example 6

In operation, the expansion of the tissue may be gradual and may be determined by the condition, body size and the breast size of the patient. The volume of gas or liquid given in one injection may be from about 25 ml to about 150 ml, for example, 50 ml. The first injection may be, for example, 50 ml and the volume may be adjusted based on the patient's condition and skin response to distention. The frequency of the injection of gas or liquid may also be adjusted depending on the patient's condition. In one embodiment, injection is done once every week. In another embodiment, for example, when a rapid expansion protocol is desired, small volumes may be injected daily, for example, about 25 ml daily for about 10 consecutive days.

Example 7

In operation, the medical device (1) may be removed from the expanded tissue using the insertion apparatus (65). The procedure includes:
  making a small incision to expose the membrane-covered port (55) of the implanted medical device (1);
  inserting the insertion apparatus (65) into the membrane-covered port (55);
  securing the insertion apparatus (65) onto the balloon (5) and the substantially hollowed core (40);
  deflating the balloon (5); and
  removing the balloon (5) from the patient.

Advantageous Effects

The embodiments described herein may be advantageous in that they require only a small incision for implanting the medical device and is minimally invasive. Performing minimally invasive procedure reduces the surgical burden imposed to the patient, including the chances of having medical complication, and the patient can recover quicker than when a larger incision is made. Because the procedure requires a minimal incision, the implanting of the medical device does not require general anesthesia. This can significantly reduce the operation time, and the procedure can be done in clinics without hospitalization, and can increase the provider efficiency. Accordingly, the medical cost for the procedure can be reduced, and breast reconstruction can be offered to patients that cannot afford the traditional implantation surgery of a tissue expander. Furthermore, as the procedure does not require using an operating room, the procedure can be offered to people living in medically under-served areas.

The embodiments described herein may be also advantageous in that they require only a small incision for removal of the medical device. The balloon may be deflated and removed without making a long incision. The benefits of using a small incision are same as described above. By combining with a permanent prosthetics that can be implanted with a small incision, the total time and cost required for breast reconstruction may be greatly reduced.

The Insertion apparatus and the shell described herein make the medical device maneuverable by touching only the handle. Therefore, the medical device is implantable without the operator directly handling the balloon. This reduces the risk of contamination during the implantation procedure and is advantageous compared to conventional large-base tissue expanders, which have larger cross-sections and require the operator to directly handle the device being implanted.

The substantially hollowed core (40) is made of a puncture proof material and prevents accidental puncturing of the balloon (5) by the insertion member (70) or the injection member (71). Thus, the chance of a failure of the medical device (1) due to leakage can be reduced.

The procedure is also advantageous in that it can be performed after the mastectomy wounds have healed. When using a traditional tissue expander, a patient had to choose whether to implant a tissue expander at the time of surgery or go through a second major surgery for the implantation. The medical device and procedure disclosed herein gives enough time for the patient to decide whether or not to receive breast reconstruction procedure and can increase the pool of candidates who might consider breast reconstruction.

The medical device disclosed herein may be used for applications other than breast reconstruction that requires tissue expansion, such as removing scars from burns, skin lesions, and injury, pigmentation, and moles. The same beneficial effect as described above for tissue expansion can be obtained using the present medical device.

I claim:
1. A medical device, comprising:
  an expandable balloon configured to be inserted into breast tissue, the balloon including:
    an inner space,
    a first longitudinal end,
    a second longitudinal end, and
    a membrane-covered port disposed at the second longitudinal end within the inner space of the expandable balloon; and
  a substantially hollowed core that is disposed in the inner space of the balloon, the substantially hollowed core including:
    an inner space,
    a first longitudinal end corresponding to the first longitudinal end of the balloon,
    a second longitudinal end corresponding to the second longitudinal end of the balloon, and a port disposed at the second longitudinal end of the substantially hollowed core, wherein the substantially hollowed core is disposed entirely in the inner space of the balloon such that the balloon is expandable along an entire length of the balloon between the first longitudinal end and the second longitudinal end of the expandable balloon that is in a shape suitable for breast reconstruction, wherein the inner space of the substantially hollowed core adjacent the first longitudinal end of the substantially hollowed core being an open lumen.

2. The medical device according to claim 1, further comprising:
an insertion apparatus having at least one insertion member and a handle,
wherein the at least one insertion member is configured to pierce the membrane-covered port and the port disposed at the second longitudinal end of the substantially hollowed core, under guidance of the handle, to enter the inner space of the substantially hollowed core,
wherein, when the insertion apparatus is engaged with the membrane-covered port and the port, the medical device is maneuverable under guidance of the handle of the insertion apparatus.

3. The medical device according to claim 2, further comprising:
a shell configured to substantially encase the balloon when the balloon is in a deflated state, the shell including:
a first longitudinal end corresponding to the first longitudinal end of the balloon,
a second longitudinal end corresponding to the second longitudinal end of the balloon, and
at least one tab disposed at the second longitudinal end of the shell,
wherein the first longitudinal end of the balloon is covered by the shell, and
wherein the shell can be separated into a first half and a second half longitudinally.

4. A method of expanding a breast tissue of a patient after a mastectomy, the method implemented by the medical device of claim 3.

5. The medical device of claim 2, wherein the handle of the insertion apparatus is configured to control removal of the medical device from the breast tissue.

6. The medical device of claim 2, wherein the at least one insertion member is configured to inject at least one of a gas or a liquid into the inner space of the substantially hollowed core.

7. The medical device of claim 2, wherein the at least one insertion member is a catheter connectable to a fluid source.

8. The medical device of claim 2, wherein the at least one insertion member is a needle connected to a fluid source.

9. The medical device according to claim 1,
wherein the substantially hollowed core includes at least one hole configured as a conduit between the inner space of the balloon and the inner space of the core,
wherein the membrane-covered port is configured to receive an injection member,
wherein the inner space of the substantially hollowed core is configured to receive at least one of a gas or a liquid through the injection member.

10. The medical device according to claim 9, wherein inner space of the substantially hollowed core is configured to receive the gas or liquid after implantation of the balloon into the breast tissue.

11. The medical device according to claim 1, wherein the balloon is expandable into a predetermined shape.

12. The medical device according to claim 1, wherein the membrane-covered port and the port are composed of a self-sealing gel and the substantially hollowed core and the expandable balloon are only connected at the second longitudinal ends of the expandable balloon and the substantially hollowed core, respectively.

13. The medical device according to claim 1, wherein the substantially hollowed core has a self-sealing gel at a middle portion of the inner space of the core, wherein the middle portion is along a longitudinal direction between the first longitudinal end and the second longitudinal end of the substantially hollowed core.

14. A method of expanding a breast tissue of a patient after a mastectomy, the method comprising:
placing a patient under local anesthesia;
making an incision that is less than about 2.0 cm into an expandable tissue of the patient;
surgically implanting the medical device of claim 1 into the expandable tissue of the patient; and
inflating the medical device gradually.

15. The medical device according to claim 1, wherein the expandable balloon has a length between 10 and 14 centimeters and a diameter of about 1 centimeter.

16. A method for breast tissue expansion of a patient, the method comprising:
implanting a medical device into a breast tissue of the patient,
wherein the medical device comprises:
an expandable balloon to be inserted into the breast tissue, the balloon including:
an inner space,
a first longitudinal end,
a second longitudinal end, and
a membrane-covered port disposed at the second longitudinal end within the inner space of the expandable balloon; and
a substantially hollowed core that is disposed in the inner space of the balloon, the substantially hollowed core including:
an inner space,
a first longitudinal end corresponding to the first longitudinal end of the balloon,
a second longitudinal end corresponding to the second longitudinal end of the balloon, and
a port disposed at the second longitudinal end of the substantially hollowed core; and
inflating the balloon with a gas and/or a liquid,
wherein the substantially hollowed core is disposed entirely in the inner space of the balloon such that the balloon is expandable along an entire length of the balloon between the first longitudinal end and the second longitudinal end of the expandable balloon that is in a shape suitable for breast reconstruction,
wherein the inner space of the substantially hollowed core adjacent the first longitudinal end of the substantially hollowed core being an open lumen.

17. The method according to claim 16, wherein the medical device further comprises:
an insertion apparatus having at least one insertion member and a handle,
wherein the at least one insertion member is configured to pierce the membrane-covered port and the port disposed at the second longitudinal end of the substantially hollowed core, under guidance of the handle, to enter the inner space of the substantially hollowed core;
a shell that substantially encases the balloon when the balloon is in a deflated state, the shell including:
 a first longitudinal end corresponding to the first longitudinal end of the balloon,
 a second longitudinal end corresponding to the second longitudinal end of the balloon, and
 at least one tab disposed at the second longitudinal end of the shell,
 wherein the first longitudinal end of the balloon is covered by the shell, and
 wherein the shell can be separated into a first half and a second half longitudinally; and
at least one hole configured as a conduit between the inner space of the balloon and the inner space of the substantially hollowed core,
 wherein the membrane-covered port is configured to receive an injection member,
 wherein the inner space of the substantially hollowed core is configured to receive the gas and/or the liquid through the injection member, and
 wherein the method further comprises:
  inserting the at least one insertion member into the balloon of the medical device via the membrane-covered port that is exposed from the shell;
  making a minimal-length incision just enough to insert the medical device into the breast tissue;
  inserting the medical device into the breast tissue of the patient by operating the handle of the insertion apparatus;
  separating the shell into the first half and the second half;
  removing the first half and the second half of the shell from the breast tissue;
  removing the insertion apparatus from the medical device;
  suturing the incision, leaving the balloon inside the breast tissue;
  inserting the at least one insertion member or an injection member into the membrane-covered port such that the at least one insertion member or the injection member connects with the inner space of the substantially hollowed core; and
  injecting the gas and/or the liquid through the at least one insertion member or an injection member into the inner space of the substantially hollowed core,
 wherein the gas or the liquid is provided from an external source.

18. The method for breast tissue expansion according to claim 17, wherein the implanting is performed without the patient being placed under general anesthesia.

19. The method of claim 16, wherein the implanting is performed concurrently with a mastectomy.

20. The method of claim 16, wherein the implanting is performed exclusive of a mastectomy.

* * * * *